United States Patent [19]

Beha

[11] Patent Number: 4,870,264
[45] Date of Patent: Sep. 26, 1989

[54] DEVICE FOR OPTICALLY MEASURING THE SHADING OF TRANSLUCENT PANES

[76] Inventor: Christian Beha, Fohrentalstrasse 6, D-7804 Glottertal, Fed. Rep. of Germany

[21] Appl. No.: 224,152
[22] Filed: Jul. 26, 1988
[51] Int. Cl.$^4$ ............................................. H01J 40/14
[52] U.S. Cl. .................................. 250/209; 356/222
[58] Field of Search ...................... 250/208, 209, 578; 356/244, 222, 224

[56] References Cited

U.S. PATENT DOCUMENTS

| 3,941,487 | 3/1976 | Ehret et al. | 356/244 |
| 3,989,948 | 11/1976 | Allington | 250/578 |
| 4,037,972 | 7/1977 | Pross | 356/206 |
| 4,236,826 | 12/1980 | Yamanishi | 356/432 |

Primary Examiner—David C. Nelms
Assistant Examiner—William L. Oen
Attorney, Agent, or Firm—Mason, Fenwick & Lawrence

[57] ABSTRACT

A device for measuring the shading of a translucent pane having an exterior side and an interior side comprising first and second photoelectric sensors for measuring unattenuated daylight, each of the sensors having a photosensitive surface and a spectral sensitivity substantially corresponding to the spectral sensitivity of the human eye and generating an output signal proportional to the intensity of the measured daylight, a first mounting element for mounting the first sensor on the exterior surface with the photosensitive surface of the first sensor facing away from the exterior surface, a second mounting element for mounting the second sensor on the interior surface with the photosensitive surface of the second sensor facing the interior surface, a housing, and an electronic circuit disposed in the housing and electrically connected to the first and second sensors for calculating the difference of the output signals of the first and second sensors, calculating the ratio of the difference to the signal from the first sensor, and displaying the ratio as a reference value.

14 Claims, 5 Drawing Sheets

DEVICE FOR OPTICALLY MEASURING THE SHADING OF TRANSLUCENT PANES

FIELD OF THE INVENTION

The invention relates to a device for measuring the shading of transparent panes or other pane-shaped objects, especially for measuring the shading of the panes of a motor vehicle.

PRIOR ART

U.S. Pat. No. 4,037,972 (Pross) describes a pocket device for measuring the transparency of a liquid to test its composition. A cell containing the liquid is inserted in the light path between a light source and a photoelectric element of the device. A second photoelectric element in the device serves as a reference for measuring the unattenuated intensity of the light source. A differential amplifier compares the light intensity measured by the true photoelectric elements.

U.S. Pat. No. 4,236,826 (Yamanishi) describes a device for measuring the optical characteristics of a pane-shaped object, especially its optical density. The subject is placed in the light path between a flashlamp source and a photodiode. The exponential decrease in light intensity from the flashlamp source is used to measure the optical density.

German Patent Application 27 57 196 describes a device for measuring the reflection and transmission of a pane-shaped object. The object is placed between photometer spheres and traversed by a beam from a light source. One photometer sphere measures the reflected intensity while the other measures the the transmitted intensity.

BACKGROUND OF THE INVENTION

Films are available on the American market which can be applied to the panes of a motor vehicle to shade said panes. The automobile owner can thus provide any shade for his vehicle panes. However, there are legal guidelines in the U.S. for the shading permitted on motor vehicle panes. To enable the police to maintain these guidelines, a device is required which can measure the shading of vehicle panes. For this purpose, the device must not require an external power source, must be lightweight and portable, and must be easy to use. In addition, the device must permit rapid reliable measurement without the policeman using the device having to get into the vehicle.

The devices known from the prior art are not suitable for this purpose. These devices require a separate light source which has a high energy consumption so that it requires an external power source. In addition, in these known devices, the pane must be located between the light source and the photoelectric element of the device so that the known devices are suitable only for measuring small samples. Finally, the attenuation of the transmitted light in the range of the spectrum that corresponds to the spectral sensitivity of the human eye is critical for the effect of the shading of the motor vehicle panes. Known devices measure an "objective" attenuation of the light in the pane while "subjective" attenuation for the human eye is important for measuring shading of the motor vehicle panes.

OBJECT OF THE INVENTION

The object of the invention is therefore a device for measuring the shading of panes, which does not require a separate light source, which permits measurement over a wide range of light intensity, which has a spectral sensitivity which corresponds to the spectral sensitivity of the human eye, which has sufficient accuracy, is designed as a pocket device, requires no external power source, and has a digital display, and which permits measurements to be made from outside the vehicle.

SUMMARY OF THE INVENTION

According to the invention a device is provided which has two photosensors, one of which is applied to the outside of the vehicle and the other, to the inside. The photosensors simultaneously measure the unattenuated daylight outside the vehicle pane and the attenuated daylight produced by the shading of the vehicle panel, inside the vehicle. The two photelectric sensors have a spectral sensitivity which corresponds to the spectral sensitivity of the human eye. Hence, the attenuation of the light intensity by the shading of the vehicle pane is measured that is effective with respect to the human eye.

The device measures daylight and therefore does not require any light source of its own. The power consumption of the device is correspondingly low, so that the device requires no external power source and can be powered by a battery.

The photoelectric sensors of the device are connected by cables to a small portable housing which contains the electronic circuit for comparing the light intensities measured by the two sensors and for the display. The two sensors are fastened by suction cups to the inside and outside of the pane. In this manner, the sensors can be mounted simply and reliably to the pane without the user of the device having to climb into the vehicle.

Since the device measures the unattenuated intensity of daylight at the outside of the pane and uses it as a reference value, the device is independent of the light intensity of the daylight, in other words, of the brightness at any given time. When the brightness of daylight fluctuates greatly, only the amplification factor of the device need be changed.

Of course, the device can be used for purposes other than measuring the shading of motor vehicle panes. It is equally suitable for measuring the shading of any transparent pane-shaped objects.

Further features and advantages of the invention will be apparent from the description which follows with reference to the drawing.

BRIEF DESCRIPTION OF THE DRAWING

FIGS. 5, 5A and 5B show the schematic of the device.

DESCRIPTION OF PREFERRED EMBODIMENT

Figure 1:
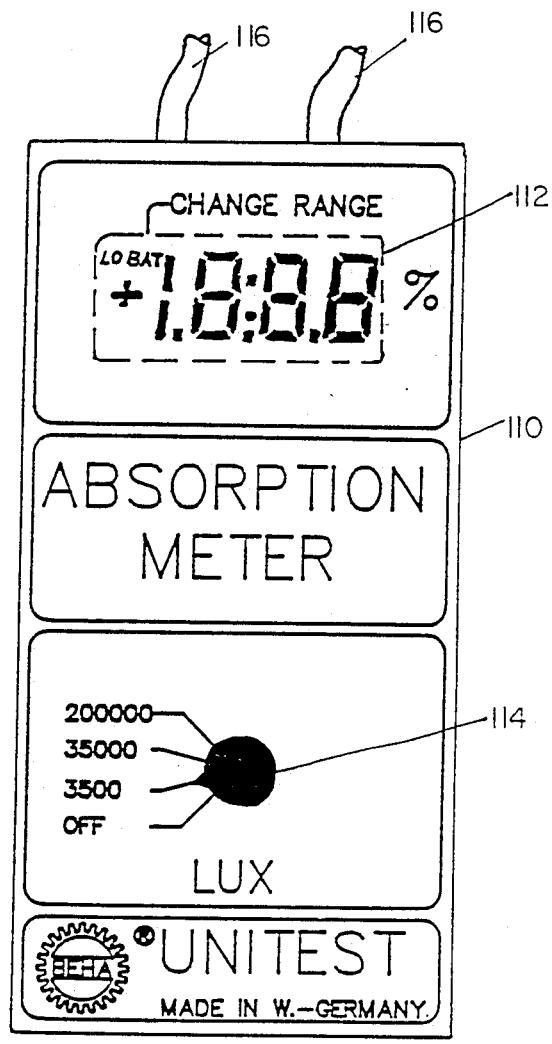
FIG. 1 shows a view of the housing of the device approximately full size.

The device in the embodiment shown in the drawing is used to measure the shading of motor vehicle panes that are coated with a shading film.

To measure the shading, one photoelectric sensor is placed outside the vehicle pane and the other, inside. The externally mounted sensor F1 measures the intensity of the illumination of the daylight striking the panel as a reference value. The internally mounted sensor F2 measures the brightness of the daylight passing through the pane and the shading film. The attenuation of the daylight passing through and hence the shading of the pane is calculated from the two measured values.

The device has a housing 110 as shown in FIG. 1. Housing 110 contains a digital LC display 112 for displaying the measured shading. The housing also contains a rotary knob switch 114 used to turn off the device and to set different light intensities for the daylight. Housing 110 is connected by cable 116 with one external photoelectric sensor F1 and one internal photoelectric sensor F2. FIG. 1 shows housing 110 on a scale of 1:1.

Figure 2:
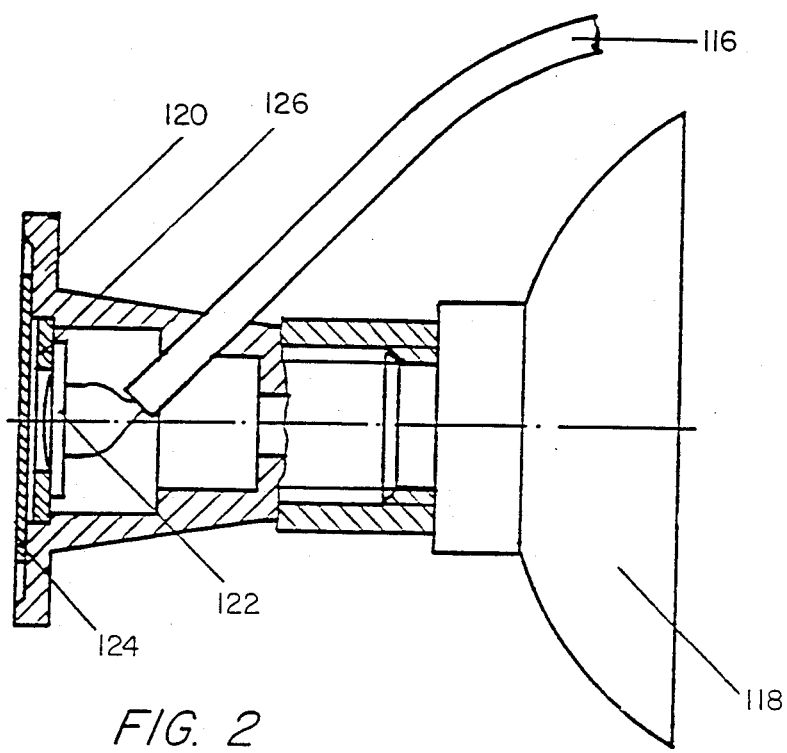
FIG. 2 is an enlarged section through the photoelectric sensor to be mounted on the outside of the motor vehicle pane.

In FIG. 2, outer photoelectric sensor F1 (and in FIG. 3, inner photoelectric sensor F2) are shown on an enlarged scale in an axial section. The sensors can use photodiodes or phototransistors. In the embodiment, sensors F1 and F2 each have a silicon-PN-planar photodiode (Telefunken model BPW21). These photodiodes have an integrated flat window with built-in color correction filter. The color correction filter adjusts the sensitivity of the photodiode to the sensitivity of the human eye in the visible range of the spectrum.

According to the legal provisions applicable in the U.S., a police officer may not enter a vehicle during the measurement. However, in order to ensure an exact measurement, the two sensors F1 and F2 must be mounted on the vehicle pane so that their light entrance angles match. For this purpose, sensors F1 and F2 are mounted on suitably long cables 116; in addition, sensors F1 and F2 can be attached to the pane with rubber suction cups. The two sensors F1 and F2 are mounted so that the outer circumferences of their respective suction cups are aligned. This ensures that the angles of incidence for the light are as similar as possible for both sensors and also that externally mounted sensor F1 does not shade internally mounted sensor F2.

As FIG. 2 shows, photoelectric sensor F1, which is to be mounted externally, has a cup-shaped rubber suction cup 118 mounted externally on the vehicle pane. A sensor receptacle 120 is mounted on the back of suction cup 118; photodiode 122 with the color correction filter is mounted in sensor receptacle 120 and covered on the side for which the light enters by a diffusing disk 124. Diffusing disk 124 homogeneously distributes the incident light flux over photodiode 122. In addition, using diffusing disk 124 lowers the spectral sensitivity of photodiode 122. Photodiode 122 therefore reacts to changes in the light ratio and slight angle changes between the two sensors F1 and F2 with less sensitivity. In addition, diffusing disk 124 absorbs the UV radiation in the daylight to a large extent so that photodiode 122 with its color correction filter is even better adapted to the sensitivity of the human eye. Cable 116 which leads to housing 110 is connected to photodiode 122 held in sensor receptacle 120 by means of a photodiode holder 126.

Figure 3:
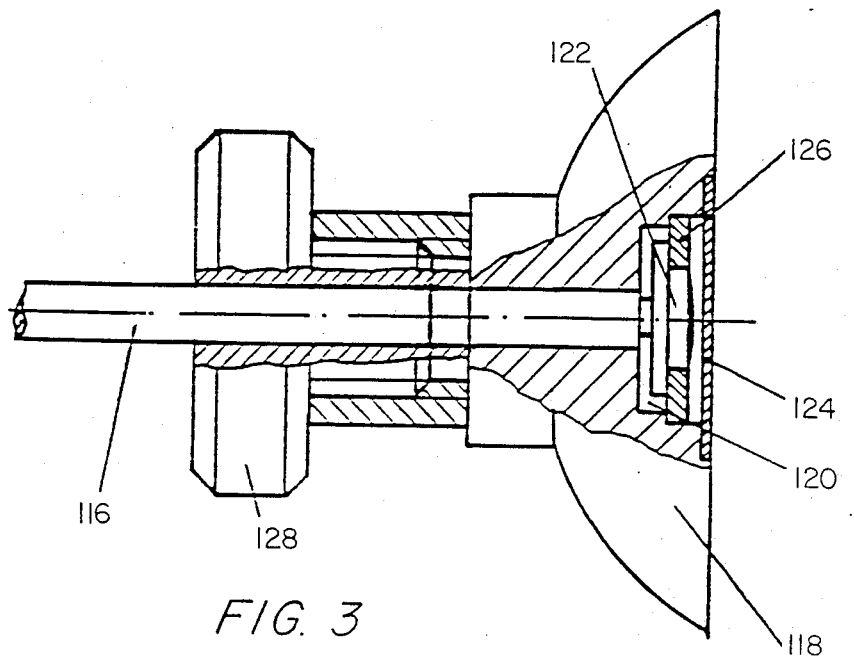
FIG. 3 shows a drawing of the sensor to be mounted on the inside of the vehicle pane.

FIG. 3 shows sensor F2 to be fastened on the inside of the vehicle pane. Sensor F2 also has a rubber suction cup 118 for fastening to the vehicle pane. However, in sensor F2 sensor receptacle 120 extends into rubber suction cup 118 so that photodiode 122 fastened by means of photodiode holder 126 and diffusing disk 124 located in front of the latter, are located in the immediate vicinity of the vehicle pane when rubber suction cup 118 is fastened to the latter. Cable 116 connected to photodiode 122 is brought out rearward from sensor receptacle 120 and held in place by means of a locking screw 128.

Figure 4:
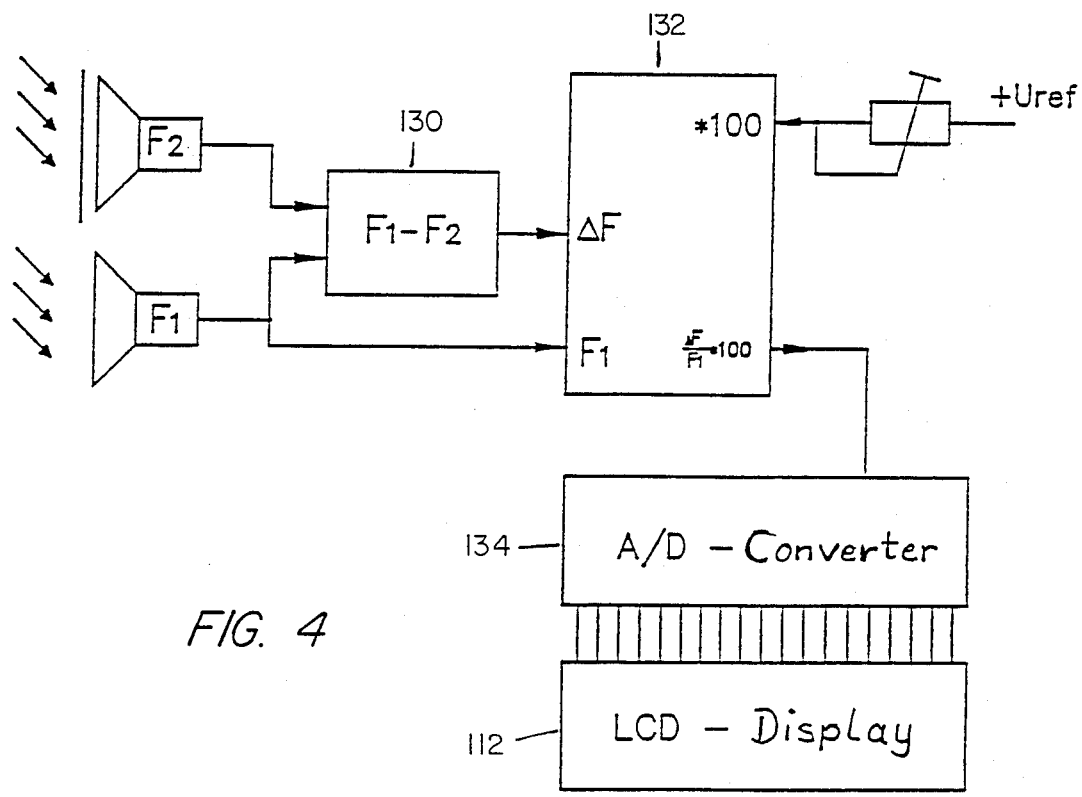
FIG. 4 is a block diagram of the device.
Figure 5A:
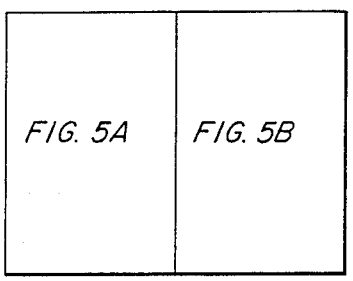
Figure 5A:
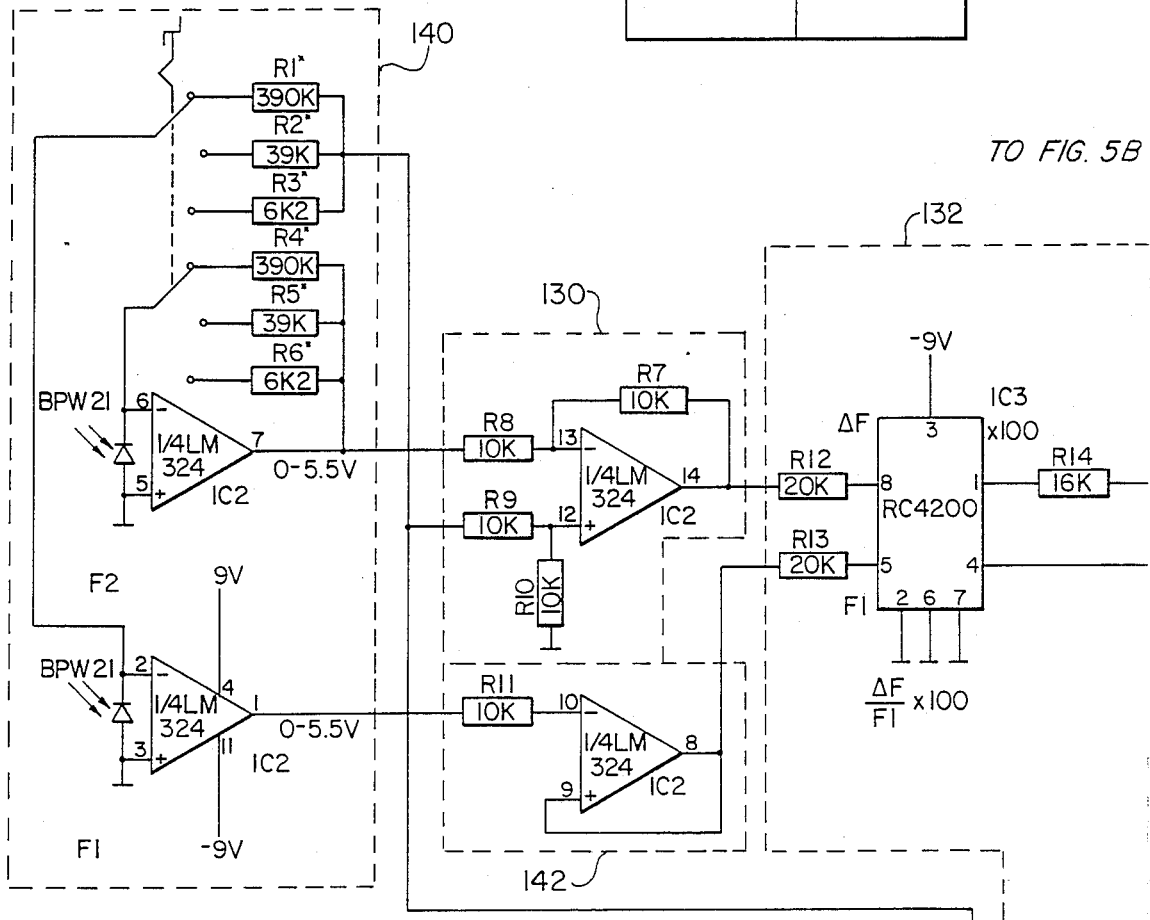
Figure 5A:
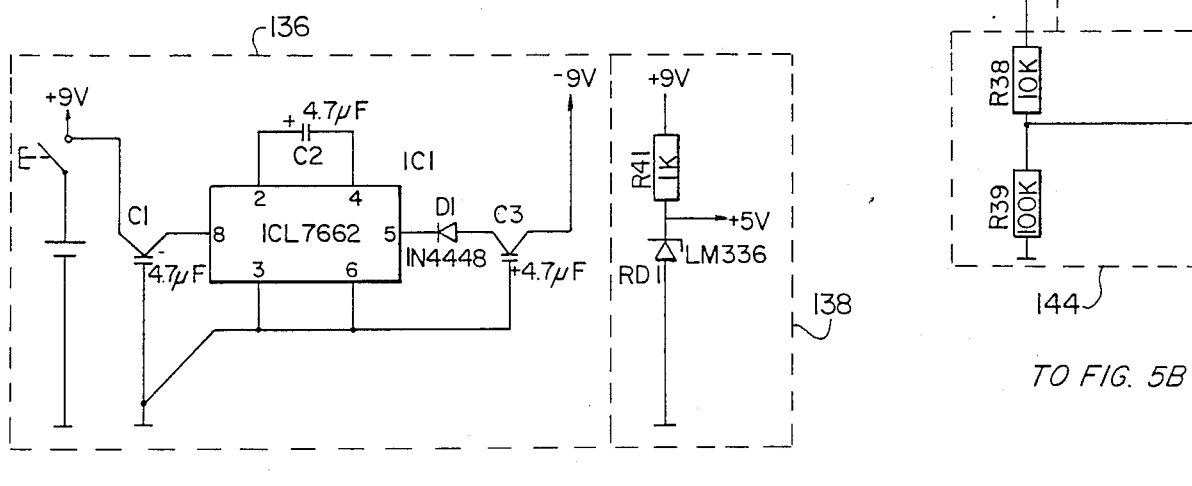
Figure 5B:
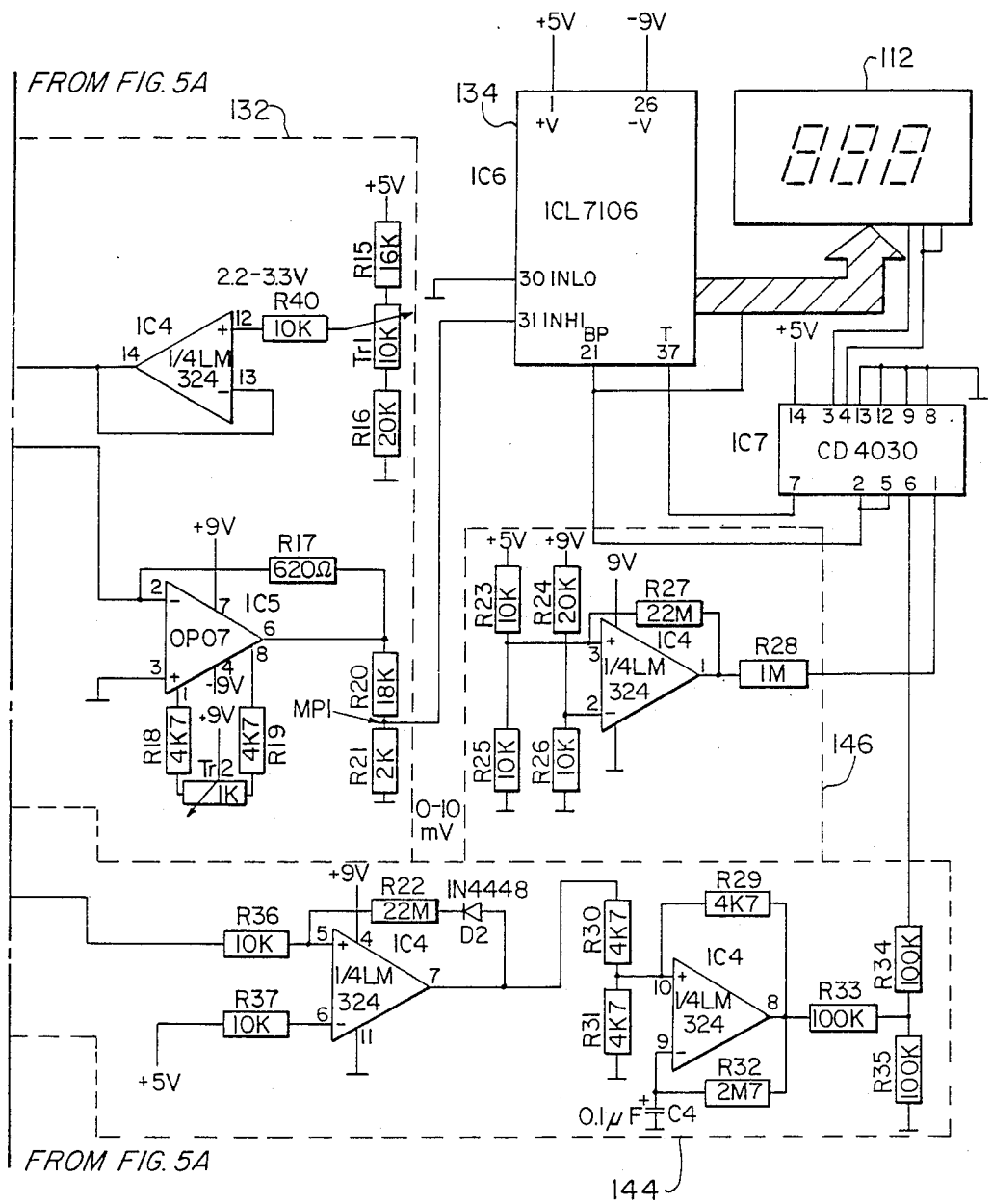

FIG. 4 shows the schematic diagram of the device and the measurement principle. The light intensities measured by outer sensor F1 and inner sensor F2 are sent to a subtracter 130 which determines the difference between the two measured values. The differential value and the measured value of outer sensor F1 are fed as a reference value to a multiplier 132. Multiplier 132 calculates the percentage attenuation of the light on passing through the shaded vehicle pane. The attenuation value, present in the form of voltage, is converted into a digital value by an analog/digital converter 134 and the value is then displayed on LC display 112.

FIG. 5 shows the entire circuit of the device in detail.

The device is powered by a 9-volt battery with a capacity of 0.5 Ah. With a current draw of approximately 15 mA for the entire circuit, the device has a maximum operating time of approximately 10 hours. If it takes about 30 seconds for one measurement, approximately 1200 measurements can be made with one battery. This means that the device requires no external power source, is easy to handle, and can be used for a very long time without changing batteries.

In order to generate the required negative voltage of $-9$ V from the supply voltage of $+9$ V of the battery, a negative voltage source 136 is provided. The circuit of negative voltage source 136 is known and uses a monolithic CMOS voltage converter (Intersil ICL 7662).

To generate an exact reference voltage for monitoring and calibrating the device, a reference voltage source 138 is provided which uses a reference diode (National Semiconductor LM 336) as the reference element.

To generate the voltage signals corresponding to the individual light intensities, which can then be processed further, a current-voltage converter 140 is used. The photodiodes (model BPW21) of the two photoelectric sensors F1 and F2 are operated without bias voltage with one operational amplifier (op amp) each ($\frac{1}{4}$ LM 324), wired as a current-voltage converter. The op amps convert the short circuit current generated by the individual photodiodes, which is proportional to the intensity of the illumination, by means of built-in feedback resistors R1 to R6 into a corresponding voltage. In order to ensure that the device will be usable at all times of day, the entire range of possible illumination intensities from 400 to 200,000 lux is covered. Three feedback resistors with values of 390 k$\Omega$ (R1 to R4), 39 k$\Omega$ (R2 to R5) and 6.2 k$\Omega$ (R3 to R6) can be switched in alternated by means of rotary knob switch 114. These different feedback resistors provide measurment ranges for illumination intensities from 400 lux to 3500 lux, from 3500 lux to 35,000 lux, and from 35,000 lux to 200,000 lux.

The two output voltage signals from current-voltage converter 140 are fed to subtracter 130. Subtractor 130 forms a difference of the voltages from the two sensors F1 and F2 by means of an op amp $\frac{1}{4}$ LM 324. Output $\Delta F$ of subtracter 130 is fed to multiplier 132 while the output of the op amp of outer sensor F1 is fed as a reference value through a voltage follower 142 to multiplier 132. Voltage follower 142 which has an op amp $\frac{1}{4}$ LM 324 ensures that the output of the op amp of outer sensor F1 is not too heavily loaded.

Multiplier 132 calculates the value ΔF/F1×100 with the aid of an analog multiplier (RC 4200) made by the Raytheon Company. This multiplier multiplies the input currents corresponding to voltage signals ΔF and 100 and divides them by the input current corresponding to the voltage signal F1. Voltage signal 100 is generated by a voltage divider and an op amp ¼ LM 324. A trim pot Tr 1 wired into the voltage divider is used for adjustment. The output current from the multiplier is converted by an op amp OP07 into a corresponding output voltage. A voltage divider with a trim pot TR2 is used to adjust the offset of the op amp.

The output voltage from multiplier 132 is fed to A/D converter 134 which converts the analog voltage value into a digital value. The A/D converter is a 3½ position monolithic A/D converter of the ICL 7106 type made by Intersil. This A/D converter is a CMOS A/D converter in which all the required active elements such as the BCD 7-segment decoder, driver stages for the display, reference voltage, and clock are all on one chip. A/D converter 134 drives LC display 112 which consists of an SP521 LC display.

If an illumination intensity range is selected while measuring using rotary knob switch 114 that results in overdriving the input amplifier, LC display 112 shows a flashing "+" symbol. An overdrive display 144 is used for this purpose. If the input stage of the current-voltage converter 140 exceeds a voltage level of 5.5 V, overdrive display 144 generates a clock frequency by which the display segments with a "+" symbol are controlled. The overdrive display consists of a comparator and a pulse generator. The comparator is formed by an op amp ¼ LM 324 which is wired as a voltage-controlled switch (Schmitt trigger) by means of a feedback to the inverting input. The output of the comparator controls the pulse generator which is in the form of a square-wave generator using an inverting voltage-controlled switch. The minus input of an op amp ¼ LM 324 is connected to a capacitor C4 for this purpose which is charged and discharged through a resistor R32 by the amplifier output. The output amplitude of the square-wave generator is fed via a voltage divider to the input of an EX-OR element (CD 4030) which controls the "+" character on LC display 112.

If the supply voltage from the battery drops below 7.5 V the display "Lo Bat" appears at the upper left of LC display 112. This is produced by a comparator circuit 146 with an op amp ¼ LM 324. The value of +5 V is used as the reference voltage. The second input voltage divider is dimensioned so that a voltage value of +5 V is applied to the minus input of the op amp below a supply voltage of 7.5 V. If the voltage drops below this value, the op amp changes its output voltage and controls the "Lo Bat" segment of LC display 112 through the EX-OR element (CD 4030).

I claim:

1. A device for measuring the shading of a translucent pane having an exterior side and an interior side, comprising:
   first and second photoelectric sensor means for measuring unattenuated daylight and attenuated daylight, respectively, and generating an output signal proportional thereto, each of said sensor means having a photosensitive surface and a spectral sensitivity substantially corresponding to the spectral sensitivity of the human eye;
   first mounting means for mounting said first sensor means on said exterior side of the pane with said photosensitive surface of said first sensor means facing away from said exterior side;
   second mounting means for mounting said second sensor means on the interior side of the pane with said photosensitive surface of said second sensor means facing the interior side;
   a housing; and
   electronic circuit means disposed in said housing and electrically connected to said first and second sensor means for calculating the difference of said output signals of said first and second sensor means, calculating the ratio of the difference of said output signals to said signal from said first sensor means, and displaying the ratio as a reference value.

2. The device of claim 1, each of said first and second sensor means comprising a photoelectric element having color correction filter means for adjusting the spectral sensitivity of said photoelectric element to the spectral sensitivity of the human eye.

3. The device of claim 2, said photoelectric element comprising a photodiode.

4. The device of claim 1, each of said first and second sensor means having a diffusing disk in front of said photosensitive surface.

5. The device of claim 1, said first and second mounting means each comprising a rubber suction cup.

6. The device of claim 1, said electronic circuit means comprising:
   a subtractor having an input and generating an output signal, said subtractor input receiving said input signals from said first and second sensors;
   a multiplier having an input and generating an output signal, said multiplier input receiving said output signal from said subtractor and said output signal from said first sensor; and
   an analog-to-digital converter having an input and generating an output signal, said converter input receiving said output signal from said multiplier.

7. The device of claim 6 said electronic circuit means comprising an LC display disposed in said housing and having an input, said display input receiving said output signal from said analog-to-digital converter.

8. The device of claim 1, further comprising first and second amplifier means for amplifying said output signals of said first and second sensor means, respectively, each of said first and second amplifier means having a switchable amplification factor.

9. The device of claim 8, further comprising a rotary knob switch operatively connected to said first and second amplifier means, said amplification factors of said first and second amplifier means being commonly switchable by said rotary knob switch.

10. The device of claim 8, further comprising:
    an overdrive display disposed in said housing and
    overdrive circuit means electrically connected to said overdrive display and said first and second amplifier means for controlling said overdrive display as soon as said first and second amplifier means are overdriven.

11. The device of claim 10, said overdrive display comprising flashing segments of and LC display controlled by said overdrive circuit means.

12. The device of claim 1, further comprising a battery disposed in said housing, said electronic circuit means being powered by said battery.

13. The device of claim 12, further comprising:
    a low battery display disposed in said housing and
    comparator circuit means for comparing the voltage of said battery with a minimum voltage and activating said low battery display as soon as the battery voltage drops below the minimum voltage.

14. The device of claim 1, said housing being pocket-sized.

* * * * *